United States Patent [19]

Bennett et al.

[11] Patent Number: 5,425,949
[45] Date of Patent: Jun. 20, 1995

[54] BIOABSORBABLE COPOLYMER AND COATING COMPOSITION CONTAINING SAME

[75] Inventors: Steven L. Bennett, Milford; Mark S. Roby, Madison; Ross R. Muth, Brookfield, all of Conn.

[73] Assignee: United States Surgical Corporation, Norwalk, Conn.

[21] Appl. No.: 75,718

[22] Filed: Jun. 11, 1993

[51] Int. Cl.⁶ ............................ A61F 2/02; A61K 47/30
[52] U.S. Cl. .................................. 424/426; 514/772.3; 514/772.6; 606/222; 606/230; 528/903
[58] Field of Search ............... 424/426; 514/772.3, 514/772.6; 606/222, 230; 528/903

[56] References Cited

U.S. PATENT DOCUMENTS

| | | | |
|---|---|---|---|
| 2,362,511 | 11/1944 | Teeters | 528/361 |
| 3,169,945 | 2/1965 | Hostettler et al. | 528/355 |
| 3,942,532 | 3/1976 | Hunter et al. | 606/231 |
| 4,605,730 | 8/1986 | Shalaby et al. | 528/357 |
| 4,624,256 | 11/1986 | Messier et al. | 606/230 |
| 4,643,191 | 2/1987 | Bezwada et al. | 606/230 |
| 4,700,704 | 10/1987 | Jamiolkowski et al. | 606/230 |
| 4,788,979 | 12/1988 | Jarrett et al. | 606/230 |
| 4,791,929 | 12/1988 | Jarrett et al. | 606/228 |
| 4,994,074 | 2/1991 | Bezwada et al. | 606/230 |
| 5,076,807 | 12/1991 | Bezwada et al. | 606/230 |
| 5,080,665 | 1/1992 | Jarrett et al. | 606/219 |
| 5,082,925 | 1/1992 | Shalaby et al. | 528/354 |
| 5,085,629 | 2/1992 | Goldberg et al. | 606/230 |
| 5,100,433 | 3/1992 | Bezwada et al. | 606/230 |
| 5,278,201 | 1/1994 | Dunn et al. | 523/113 |

*Primary Examiner*—Gollamudi S. Kishore
*Assistant Examiner*—Carlos Aspuru

[57] ABSTRACT

A bioabsorbable copolymer is obtained from the polymerization of a major amount of ε-caprolactone and a minor amount of at least one other copolymerizable monomer in the presence of an initiator possessing at least two carboxylic acid groups. The copolymer is useful, inter alia, as a coating for a surgical suture.

8 Claims, No Drawings

BIOABSORBABLE COPOLYMER AND COATING COMPOSITION CONTAINING SAME

BACKGROUND OF THE INVENTION

This invention relates to a bioabsorbable copolymer and, more particularly, to a bioabsorbable copolymer obtained by polymerizing a major amount of ε-caprolactone and a minor amount of at least one other copolymerizable monomer in the presence of an initiator possessing at least two carboxylic acid groups.

U.S. Pat. No. 2,362,511 discloses a polyglycolide resin derived from glycolide and from about 20 to about 55 weight percent of a carboxylic acid such as lactic acid, tartaric acid, malic acid, citric acid, etc.

U.S. Pat. No. 3,169,945 discloses a homopolymer of ε-caprolactone obtained by polymerizing ε-caprolactone in the presence of a carboxylic acid initiator such as citric acid, aconitic acid, mellitic acid, pyromellitic acid, etc.

U.S. Pat. No. 3,942,532 discloses a surgical suture coating composition comprising a polyester derived from the esterification of a low molecular weight glycol and a dimeric acid such as succinic acid, glutaric acid, adipic acid, etc.

U.S. Pat. No. 4,624,256 discloses a bioabsorbable copolymer derived from at least 90 weight percent of ε-caprolactone and up to 10 weight percent of a carboxylic acid such as glycolic acid, lactic acid, malic acid, succinic acid, etc.

U.S. Pat. No. 4,643,191 discloses a copolymer obtained by: (1) the polymerization of p-dioxanone in the presence of a carboxylic acid initiator such as glycolic acid, lactic acid, etc., to form a mixture of p-dioxanone monomer and homopolymer and (2) subsequent polymerization of (1) with lactide to form the copolymer.

U.S. Pat. No. 5,076,807 discloses a bioabsorbable copolymer derived from polymerizing p-dioxanone and glycolide in the presence of a carboxylic acid initiator, e.g., glycolic acid or lactic acid.

Copolymers derived from ε-caprolactone and at least one other monomer such as lactide, glycolide, glycolic acid, p-dioxanone and trimethylene carbonate are disclosed in U.S. Patent Nos. 4,605,730, 4,624,256, 4,700,704, 4,788,979, 4,791,929, 4,994,074, 5,076,807, 5,080,665, 5,085,629 and 5,100,433.

SUMMARY OF THE INVENTION

In accordance with the present invention, a bioabsorbable copolymer is obtained by polymerizing a major amount of ε-caprolactone and a minor amount of at least one other copolymerizable monomer in the presence of an initiator possessing at least two carboxylic acid groups.

The particular structure of the bioabsorbable copolymer herein exerts a characteristic influence on its bioabsorption behavior making it useful, among other applications, as a surgical suture coating material.

DESCRIPTION OF THE PREFERRED EMBODIMENTS

Conventional polymerization techniques that are well known and disclosed in the prior art can be utilized in preparing the bioabsorbable copolymer of the present invention. The bioabsorbable copolymer is obtained by polymerizing a major amount of ε-caprolactone and a minor amount of at least one other copolymerizable monomer in the presence of a carboxylic acid initiator having at least two carboxylic acid groups. The polymerization of these monomers contemplates all of the various types of monomer addition, i.e., simultaneous, sequential, simultaneous followed by sequential, sequential followed by simultaneous, etc.

Suitable monomers which can be copolymerized with ε-caprolactone include glycolide, lactide, p-dioxanone and trimethylene carbonate.

Suitable carboxylic acid initiators include succinic acid, maleic acid, glutaric acid, adipic acid, pimelic acid, suberic acid, azelaic acid, sebacic acid, malic acid, tartaric acid, citric acid, aconitic acid, pyromellitic acid, mellitic acid, etc., and combinations thereof.

The copolymer herein can contain from about 70 to about 98, and preferably from about 80 to about 95, weight percent ε-caprolactone-derived units, the balance of the copolymer being derived from the other copolymerizable bioabsorbable monomer(s). The inherent viscosity of the copolymer generally ranges from about 0.05 to about 0.35, and preferably from about 0.15 to about 0.25, dl/g when measured in chloroform at a concentration of 0.2500 g/dl at 30° C. The carboxylic acid initiator is generally employed in small amounts, e.g., from about 0.5 to about 5, and preferably from about 0.1 to about 2, weight percent of the total monomer mixture.

The bioabsorbable copolymer of the present invention is non-toxic and physiologically inert. Depending on its particular physical and bioabsorption properties (to a large extent influenced by the nature of the initiator and monomers from which it is prepared), the bioabsorbable copolymer herein can be used in the fabrication in whole or in part of a variety of implantable medical devices and prostheses, e.g., clips, staples, sutures, suture coatings, etc. Applied to a suture, a coating composition containing the bioabsorbable copolymer of the invention results in a significant improvement in one or more properties of the suture, e.g., its lubricity, knot tiedown and/or knot security characteristics.

The bioabsorbable copolymer of the invention can be applied to a suture by any suitable process, e.g., passing the suture through a solution of the copolymer, e.g., in acetone, methylene chloride, etc., past a brush or other coating solution applicator, or past one or more spray nozzles dispensing the suture coating solution. The suture wetted with the coating solution is subsequently passed through or held in a drying oven for a time and at a temperature sufficient to vaporize and drive off the solvent. If desired, the suture coating composition can optionally contain additional components, e.g., dyes, antibiotics, antiseptics, growth factors, anti-inflammatory agents, etc.

While the coating composition herein can be applied to any type of suture, it is essentially intended for application to a braided suture, a preferred type of which is disclosed in U.S. Pat. No. 5,019,093, the contents of which are incorporated by reference herein. The amount of coating composition applied to a braided suture will vary depending upon the structure of the suture, e.g., the number of filaments, tightness of braid or twist, the size of the suture and its composition.

The coating composition herein can be used for both "unfilled" as well as "filled" sutures, the latter designating braided bioabsorbable sutures containing a storage stabilizing material as disclosed in U.S. Pat. Nos. 5,037,429 or 5,051,272, the contents of which are incorporated by reference herein. For an "unfilled" suture, the coating composition can be applied at a level of from about 0.5 to about 4 weight percent or more and preferably from about 1 to about 3 weight percent. Advantageously, the coating composition is applied to the suture prior to application of the storage stabilizing material. For a filled suture, the amount of applied coating composition can range from about 0.2 to as much as about 3 weight percent or more and preferably from about 0.5 to about 2 weight percent. As a practical matter, it is generally preferred to apply the minimum amount of coating composition consistent with good tie-down performance. This level of coating add-on can be readily determined for any particular suture coating system employing routine experimental procedures.

In the case of an unfilled or filled braided suture, prior to application of the coating composition, it can be advantageous to calender the suture in order to improve the uniformity with which the coating composition is laid down upon the suture surface. A calendering operation can also be beneficial when carried out on a coated suture where the suture is to be filled with a storage stabilizing material. In this case, calendering will tend to break up the coating facilitating penetration of the interior spaces of the suture by the storage stabilizing material.

A preferred method for calendering a braided suture and an apparatus for carrying out the method are disclosed in copending U.S. patent application Ser. No. 07/652,939, filed Feb. 8, 1991, the contents of which are incorporated by reference herein. In accordance with Ser. No. 07/652,939, calendering of a braided suture is achieved by applying a compressive force to the suture in a first line or direction generally transverse to the longitudinal direction of the suture, the compressive force being of sufficient magnitude as to flatten the suture in a direction orthogonal to the direction in which the compressive force is applied. Preferably, a second application of compressive force is applied to the suture in a direction generally transverse to that of the first compressive force and transverse to the longitudinal direction of the suture. The second compressive force is substantially equal in magnitude to the first compressive force so that the suture returns to its original cross-sectional configuration.

The apparatus for implementing the foregoing calendering method includes at least one pair of rollers which are biased towards each other to apply a compressive force to the suture as the suture passes between them. Optionally, a second pair of rollers is provided which is oriented at an angle (preferably 90°) to the first pair of rollers and transverse to the longitudinal direction of the suture. Following passage between both the first and second pair of rollers, the suture will have been alternately compressed, or flattened, in a first direction and thereafter in a second direction at an angle to the first direction.

The following examples are illustrative of the bioabsorbable copolymer of this invention, its preparation and its application as a coating to sutures.

EXAMPLES 1-3

In three separate polymerizations, ε-caprolactone (67.5 g), glycolide (7.5 g), stannous octate as catalyst (0,015 g) and citric acid (3.0 g) (Example 1), mallic acid (3.0 g) (Example 2) and tartaric acid (3.0 g) (Example 3) as initiators were mixed under nitrogen for one hour and thereafter copolymerized in a reactor at 160° C. for 24 hours. In each polymerization, greater than 95 weight percent conversion of monomers to copolymer was achieved.

The inherent viscosities of the copolymers, which were measured in $CHCl_3$ at a concentration of 0.2500 g/dl at 30° C., were as follows:

| Example | Initiator | Inherent Viscosity (dl/g) |
| --- | --- | --- |
| 1 | Citric acid | 0.17 |
| 2 | Mallic acid | 0.16 |
| 3 | Tartaric acid | 0.22 |

EXAMPLES 4-16; COMPARATIVE EXAMPLES 1-6

Performance characteristics of size 0 sutures coated with the acid-initiated ε-caprolactone-glycolide copolymers of Examples 1-3 were measured. Sutures coated with another coating composition, i.e., a block copolymer wherein polypropylene glycol comprises one block and a glycolide-lactide copolymer comprises the other block, were similarly tested for comparative purposes. The coating level of copolymer on each suture, expressed in terms of percent by weight of the suture, was determined by NMR. After coating a suture with a solution of copolymer and subsequently drying the suture in an oven for 96 hours, the suture was tested on a tie board to evaluate certain of its performance characteristics, i.e., surgeon's throw, knot reposition and knot security.

A tie board consists of a base on which two plates are perpendicularly affixed. These plates are parallel to one another on the base and are separated by a distance of at least 3 inches. Each plate contains two oppositely disposed openings, the distance between the openings on one plate being longer than that of the other plate. An elastic tube is passed through the openings on both plates to complete a loop which is then tied to secure the loop to the plates. The loop is in the general configuration of an isosceles triangle. To perform the Surgeon's Throw and Knot Reposition tests as described below, a suture is looped around the elastic tube of the tie board and tied. The elastic tube exerts an outward force on the suture knot. This force approximates the force exerted by living tissue on suture knots. Thus, the tie board is an effective means of evaluating the performance characteristics of surgical sutures.

The procedures for evaluating these performance characteristics are described in Table I as follows:

TABLE I

PROCEDURES FOR MEASURING PERFORMANCE CHARACTERISTICS OF SUTURES COATED WITH ε-CAPROLACTONE-GLYCOLIDE COPOLYMERS

| Performance Characteristics | Test Procedure |
| --- | --- |
| Surgeon's Throw | A suture is looped around the elastic tubes of a tie board and tied with a surgeon's throw (a half hitch with an extra loop of the free end). The ends are pulled apart by hand and the suture loop pulls the elastic tubes of the tie board together. The ends of the suture are then released. If the tubes stay together for approximately ten seconds, the trial is counted as a "pass". If the surgeon's throw slips and the tubes move apart, the trial is counted as a "failure". |
| Knot Reposition | A suture is looped around the elastic |

TABLE I-continued

PROCEDURES FOR MEASURING PERFORMANCE CHARACTERISTICS OF SUTURES COATED WITH ε-CAPROLACTONE-GLYCOLIDE COPOLYMERS

| Performance Characteristics | Test Procedure |
|---|---|
| | tubes of a tie board and tied with two half hitches in the same direction (a granny knot). The free ends of the suture are pulled apart by hand. If the knot slips and the loop of the suture pulls the elastic tubes of the tie board together, the knot is said to reposition and the trial is counted as a "pass". If the suture breaks or if the knot locks in place and cannot be moved, the trial is counted as a "failure". |
| Knot Security | A 2 cm loop is tied with a surgeon's square knot (1 = 1 = 1 = 1) securing the throws at 20% of the USP XXII knot strength for 2/0 nonabsorbable sutures (n = 10 loops per group). The loop is placed next to a cloth-wrapped mandrel rotating at .5 rpm. The fixtures are secured to allow contact of the cloth material against the fourth throw or, top throw, of each knot. The cloth wrapping is moistened with 37° C. water prior to the test and is periodically remoistened during the test. For each pass of the cloth across the knot (for a total of 100 passes), the knot is inspected for top throw security. For a knot to be considered secure, there must be no relaxation of the knot or loss of the fourth throw. |
| In vitro degradation (100° C./48 hours) | A suture was immersed in boiling water for 48 hours and thereafter weighed to determine the amount of weight loss |

The results of these tests are set forth in Table II as follows:

TABLE II

PERFORMANCE CHARACTERISTICS OF SUTURES COATED WITH ε-CAPROLACTONE-GLYCOLIDE COPOLYMERS AND POLYPROPYLENE GLYCOL/GLYCOLIDE-LACTIDE BLOCK COPOLYMER

| | Initiator* | Coating Level (%) | Surgeon's Throw (No. passes out of 10 attempts) | Knot Reposition (No. passes out of 10 attempts) | Knot Security (No. throws to secure) | In Vitro Degradation (100° C./48 hours) |
|---|---|---|---|---|---|---|
| Example | | | | | | |
| 4 | CA | 0.7 | 8 | 10 | 3 | 33 |
| 5 | CA | 1.1 | 7 | 10 | 4 | — |
| 6 | CA | 1.5 | 7 | 10 | 3 | — |
| 7 | CA | — | 5 | 10 | — | — |
| 8 | CA | 2.9 | 7 | 10 | — | — |
| 9 | MA | 0.8 | 10 | 10 | 3 | 29 |
| 10 | MA | 1.3 | 9 | 9 | 3 | — |
| 11 | MA | 1.6 | 6 | 9 | 3 | — |
| 12 | MA | — | 6 | 6 | — | — |
| 13 | MA | — | 3 | 9 | — | — |
| 14 | TA | 0.8 | 7 | 10 | 3 | 35 |
| 15 | TA | 1.1 | 5 | 10 | 4 | — |
| 16 | TA | 1.6 | 9 | 10 | 4 | — |
| Comparative Example | | | | | | |
| 1 | — | — | 7 | 7 | 4 | — |
| 2 | — | — | 2 | 10 | — | — |
| 3 | — | — | 8 | 7 | — | — |
| 4 | — | — | 6 | 8 | — | — |
| 5 | — | — | 10 | 8 | — | — |
| 6 | — | — | 8 | 8 | 3 | — |

*CA = citric acid. MA = mallic acid and TA = tartaric acid.

As the foregoing data show, sutures coated with the copolymers of this invention possess performance characteristics that are equal or superior to those of the Comparative Example. In particular, the knot reposition characteristics of sutures coated with the copolymers of this invention (Examples 4–16) are excellent, i.e., a rating of 10 successful passes out of 10 attempts was obtained for 9 out of 13 coated sutures which were tested.

What is claimed is:

1. A surgical suture coated with a coating composition comprising a bioabsorbable copolymer obtained by polymerizing a major amount of ε-caprolactone and a minor amount of bioabsorbable monomer in the presence of an initiator possessing at least two carboxylic acid groups, wherein the copolymer possesses from about 70 to about 98 weight percent ε-caprolactone-derived units and an inherent viscosity of from about 0.05 to about 0.35 dl/g when measured in chloroform at a concentration of 0.2500 g/dl at 30° C., the initiator possessing at least two carboxylic acid groups is employed in an amount of from about 0.5 to about 5 weight percent of the total monomer mixture and the coating composition is applied to the suture at a level of from about 0.1 to about 5 weight percent of the entire coated suture.

2. The surgical suture of claim 1 which is a bioabsorbable braided suture.

3. The suture of claim 1 wherein the bioabsorbable monomer is selected from the group consisting of glycolide, lactide, p-dioxanone and trimethylene carbonate.

4. The suture of claim 1 wherein the initiator is selected from the group consisting of succinic acid, maleic acid, glutaric acid, adipic acid, pimelic acid, suberic acid, azelaic acid, sebacic acid, malic acid, tartaric acid, citric acid, aconitic acid, pyromellitic acid and mellitic acid.

5. The suture of claim 1 wherein the copolymer contains from about 80 to about 95 weight percent ε-caprolactone-derived units, the balance of the copolymer being derived from the bioabsorbable monomer(s).

6. The suture of claim 1 wherein the copolymer possesses an inherent viscosity from about 0.15 to about 0.25 dl/g when measured in chloroform at a concentration of 0.2500 g/dl at 30° C.

7. The suture of claim 1 wherein the initiator is employed in an amount of from about 0.1 to about 2 weight percent of the total monomer mixture.

8. The suture of claim 1 wherein the coating composition is applied to a suture at a level of from about 0.5 to about 2.5 weight percent of the entire coated suture.

* * * * *